US010030888B2

(12) United States Patent
Dumitrescu (10) Patent No.: US 10,030,888 B2
(45) Date of Patent: Jul. 24, 2018

(54) METHODS, SYSTEMS, AND APPARATUS PROVIDING A TEMPERATURE-CONTROLLED PROCESS LIQUID

(71) Applicant: Nicolae Dumitrescu, Stamford, CT (US)

(72) Inventor: Nicolae Dumitrescu, Stamford, CT (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/400,294

(22) PCT Filed: May 8, 2013

(86) PCT No.: PCT/US2013/040051
§ 371 (c)(1),
(2) Date: Nov. 10, 2014

(87) PCT Pub. No.: WO2013/169841
PCT Pub. Date: Nov. 14, 2013

(65) Prior Publication Data
US 2015/0323220 A1    Nov. 12, 2015

Related U.S. Application Data

(60) Provisional application No. 61/645,654, filed on May 11, 2012.

(51) Int. Cl.
*F24H 1/12* (2006.01)
*G05D 23/19* (2006.01)
(Continued)

(52) U.S. Cl.
CPC ........... *F24H 1/12* (2013.01); *G01N 35/1016* (2013.01); *G05D 23/1919* (2013.01); *G01N 35/0099* (2013.01); *G01N 2035/00346* (2013.01)

(58) Field of Classification Search
CPC ................. F24H 1/10; F24H 1/12; F24H 1/14
See application file for complete search history.

(56) References Cited

U.S. PATENT DOCUMENTS 4,367,198 A * 1/1983 Scordato ................... B01L 7/00
220/501
6,182,453 B1    2/2001 Forsberg
(Continued)

FOREIGN PATENT DOCUMENTS

| WO | 1987003966 A1 | 7/1987 |
| WO | 2010075199 A2 | 7/2010 |
| WO | 2012009213 A1 | 1/2012 |

OTHER PUBLICATIONS

PCT International Search Report and Written Opinion dated Oct. 22, 2013 (13 Pages).

*Primary Examiner* — Brian R Gordon (57) ABSTRACT

Disclosed are systems and apparatus adapted to control a temperature of a process liquid in a metering line of an instrument. In one aspect, a temperature-controlled liquid delivery apparatus has a pre-flux member operable to control a first temperature set point SP1 of the process liquid in a flow path between a feed tank and a metering apparatus, a metering line connecting the metering apparatus and a probe, and a line flux member directly thermally coupled to the metering line and operable to control a second temperature set point SP2 of the process liquid contained in the metering line. Methods of operating the system are provided, as are other aspects.

19 Claims, 4 Drawing Sheets (51) Int. Cl.
*G01N 35/10* (2006.01)
*G01N 35/00* (2006.01)

(56) References Cited

U.S. PATENT DOCUMENTS

| | | |
|---|---|---|
| 6,311,868 B1 | 11/2001 | Krietemeier et al. |
| 6,989,131 B2 * | 1/2006 | Karlsson .............. B01J 19/0046 422/501 |
| 2001/0020396 A1 | 9/2001 | Zeller |
| 2008/0078694 A1 | 4/2008 | Sexton et al. |
| 2010/0066374 A1 | 3/2010 | Trygstad et al. |
| 2012/0024892 A1 | 2/2012 | Bartlett et al. |

\* cited by examiner

METHODS, SYSTEMS, AND APPARATUS PROVIDING A TEMPERATURE-CONTROLLED PROCESS LIQUID

FIELD

The present invention relates generally to methods, systems, and apparatus adapted to provide a temperature-controlled process liquid.

BACKGROUND

In medical specimen testing, purified water may be dispensed for various purposes. In certain clinical analyzer instruments used to test for the presence of an analyte in a biological fluid sample (otherwise referred to as "specimens"), it may be desirable to precisely meter water to be used in the process. For example, in some automated testing systems (e.g., clinical analyzer or immunoassay instruments), specimens contained in sample containers (such as test tubes, sample cups, vials, cuvettes, and the like) may be tested to determine a presence of a particular analyte, substance, or characteristic. As part of this testing process, precise metering of a process liquid (e.g., purified water) and/or control of a temperature of the process liquid may be desired in order to provide for testing accuracy.

For example, in some testing methods, such as the so-called "chase method," a volume of specimen liquid is first aspirated and dispensed by a metering apparatus, and the dispensing of this specimen liquid is followed (chased) by dispensing a metered volume of a process liquid (e.g., purified water). In the chase method, the volume of dispensed process liquid may be greater than the volume of the specimen liquid that is dispensed. In the so-called "neat method," a small amount of specimen liquid is aspirated and dispensed (on the order of less than about 10 μL). In the neat method, the process liquid itself (e.g., purified water) may be the vehicle (e.g., the liquid backing) that allows for the metering of the specimen liquid, even though the process liquid (e.g., purified water) may not itself dispensed in the neat method. However, for both methods, it should be understood that inaccurate metering and/or changes in the temperature of the process liquid may lead to inaccurate specimen testing results.

Accordingly, methods, systems, and apparatus that may improve aspiration and/or dispensing of a process liquid (e.g., purified water) or other liquids are desired.

SUMMARY

According to a first aspect, a temperature-controlled process liquid delivery system is provided. The process liquid delivery system includes a feed tank containing a process liquid, a metering apparatus fluidly coupled to the feed tank, the metering apparatus adapted to meter the process liquid, a pre-flux member positioned between the feed tank and the metering apparatus and adapted to control a temperature of the process liquid received at the metering apparatus, a probe fluidly coupled to the metering apparatus by a metering line, and a line flux member directly thermally coupled to the metering line and adapted to control a temperature of the process liquid contained in the metering line.

According to another aspect, a temperature-controlled liquid delivery apparatus is provided. The liquid delivery apparatus includes a metering apparatus, a probe, a pre-flux member operable to control a temperature of a process liquid contained in a flow path between a feed tank and the metering apparatus, a metering line connected between the metering apparatus and the probe, and a line flux member directly thermally coupled to the metering line and operable to control a temperature of the process liquid contained in the metering line.

In a method aspect, a method of providing a temperature-controlled process liquid is provided. The method includes providing a liquid delivery apparatus having a pre-flux member thermally coupled to a flow path containing a process liquid and located between a feed tank and a metering apparatus, a metering line containing the process liquid connected between the metering apparatus and a probe, and a line flux member directly thermally coupled to the metering line, and controlling at least one of a first temperature set point SP1 of the pre-flux member and a second temperature set point SP2 of the line flux member, or both, to control a temperature of the process liquid at an exit of the metering line.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

DETAILED DESCRIPTION

For at least the above-described reasons, achieving precision in the metering of a process liquid and/or improving control of a temperature thereof in medical specimen testing is desirable. In one or more assay tests, temperature drift of the process liquid and/or metering error in some metering apparatus and systems may be attributed to changes in a temperature of the process liquid that is contained within a metering line extending between a metering apparatus (e.g., including a pump) and a probe (e.g., sample probe). In some embodiments, such as in acridinium ester assays, temperature drift in one or more of the liquid components involved in the assay due to environmental temperature change within the operational temperature range may affect testing results. In other embodiments, variations in a temperature of the process liquid (e.g., purified water) that is contained in the metering line over time may affect a volume of the process liquid dispensed. Additionally, in cases where a secondary liquid is dispensed (e.g., a biological liquid specimen such as blood, serum/plasma, urine, spinal fluid, cerebral fluid, interstitial fluid, or the like) but where the process liquid is fluidly coupled to the secondary liquid as a liquid backing, any expansion or contraction of the process liquid in the metering line may likewise affect the level of precision achievable when metering of the secondary liquid, even though none of the process liquid may be dispensed. Also, changes in temperature of the backing liquid may affect the dispensed temperature of any liquid aspirated (e.g., reagent, biological liquid, or the like). At the same time the temperature of the process liquid acting as a backing liquid may be affecting the temperature of the probe and any liquid (e.g., biological liquid specimen, liquid reagent, or the like) that is being aspirated. The probe is washed in a probe washing operation before every biological liquid specimen is aspirated. A large volume (e.g., 21,000 µl) of process liquid may be flushed through the metering line and probe while the probe is inside a washing station. During the probe wash operation, the temperature of the probe and the metering line may be influenced by the controlled temperature of the process liquid. By controlling the temperature of the process liquid that is being dispensed, liquid temperature of the dispensed liquid (e.g., biological liquid, reagent, or the like) may also be controlled. Therefore, the temperature of the process liquid may be used to compensate for environmental temperature changes under the housing of the instrument.

For example, if a biological liquid specimen aspirated from a sample liquid to be tested is provided within an end of the probe that is at one temperature, the temperature of the probe will influence the temperature of the biological liquid specimen. Likewise, if the liquid is refrigerated (e.g., refrigerated liquid reagent) then the aspirated liquid reagent may also be influenced by the temperature of the probe. Because the process liquid may be contained in the metering line for a relatively longer period of time, it may also be subject to appreciable temperature variations over time. Accordingly, temperature variations over time may contribute to environmental drift in certain testing (e.g., assays) and may contribute to testing inaccuracies. Also, volumetric expansion and contraction of the process liquid contained in the metering line may contribute to testing inaccuracies.

In some instances, such as those where the metered volume of the biological liquid specimen is quite small (such as in the above-mentioned "neat method"), the contribution of liquid expansion and/or contraction of the process liquid in the metering line over time may affect the overall testing accuracy. However, environmental temperature drift in certain testing (e.g., assays) may contribute to testing inaccuracies. In other assays where the volume dispensed is relatively large, environmental temperature drift may be a dominant factor in achieving testing accuracy. Previous methods have overcome these inconsistencies by performing relatively frequent recalibrations of the liquid delivery system. However, such calibrations can be quite time intensive, and may take away from time that the testing system may be used for carrying out diagnostic testing. Accordingly, better methods and apparatus for accounting for and correcting metering line temperature changes and ensuring sufficient testing accuracy due to system temperature fluctuations are sought.

Figure 1:
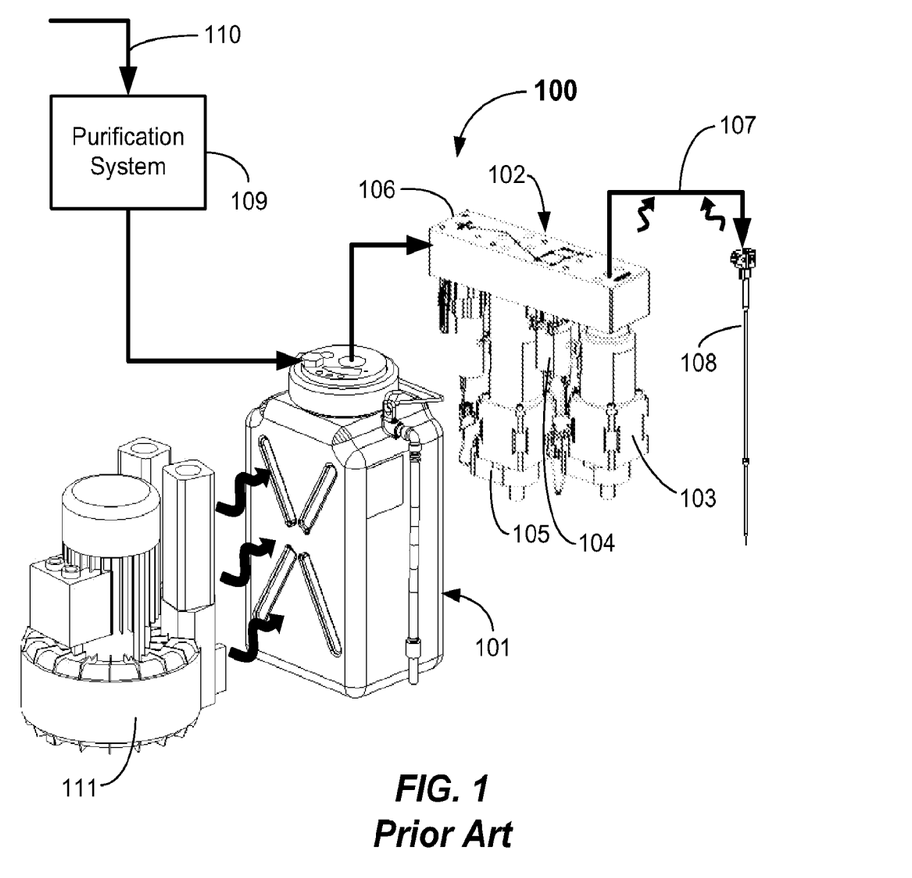
FIG. 1 illustrates a diagram of a process liquid delivery system according to the Prior Art.

As shown in FIG. 1, a prior art liquid delivery system 100 includes a feed tank 101, which provides a supply of purified water to a metering apparatus 102 including a metering pump 103 for metering small volumes, one or more valves 104, a flush pump 105 for metering relatively larger volumes of liquid, a distribution manifold 106, and a metering line 107 coupled to a probe 108. The metering line 107 fluidly couples the probe 108 to the distribution manifold 106 so that aspirating and dispensing liquids may take place. The feed tank 101 in the prior art liquid delivery system 100 is filled from a purification system 109, which receives an inflow of process liquid (e.g., water) directly from a water supply 110, such as a municipal water supply, for example.

Temperature variations experienced in the metering line 107 may come from multiple sources. For example, in some instances, steady use may contribute to temperature variations (e.g., system temperature increases over time), which may arise from heat being transferred by convection, conduction, and/or radiation from other system components, such as the vacuum pump 111 shown or other components. Additional temperature variations may come from intermittently filling of the feed tank 101 with relatively cooler water from the purification system 109 for example. This variation in temperature may be especially prevalent at times of high usage of the liquid delivery system 100. Other contributors may be due to changes in temperature of the water supply 110 (e.g., daily or seasonal changes in water supply temperature), starting and stopping the system 100, and changes in ambient temperature to which the system 100 is exposed.

Variations in temperature of the inflow water from the water supply 110 provided to the purification system 109 may produce temperature variations at the feed tank 101, at the pumps 103, 105, at the probe 108, and in the metering line 107 over time. Such temperature changes over time may result in contraction and/or expansion of the process liquid (e.g., purified water) contained in the metering line 107. As stated, this relative change in liquid volume in the metering line 107 may affect metering accuracy over time. Such inaccuracies in metering may lead to inaccuracies in the testing results. However, because certain accuracies are desired in the prior art liquid delivery system, more frequent re-calibration processes may take place in order to ensure that a desired level of accuracy is achieved.

In view of the foregoing problems, embodiments the present invention provide methods, systems, and apparatus that are adapted to control a temperature of a process liquid contained in the metering line. In particular, it may be desired to control the temperature in the metering line at its exit to within limits. According to one or more embodiments of the invention, in some instances, this may involve controlling a temperature of the process liquid at multiple locations within the system. Controlling a temperature of the process liquid at the multiple locations may be used to more precisely control a temperature of the process liquid provided at an exit from the metering line (such as at the probe).

These and other aspects and features of embodiments of the invention will be described with reference to FIGS. 2-5 herein.

Figure 2:
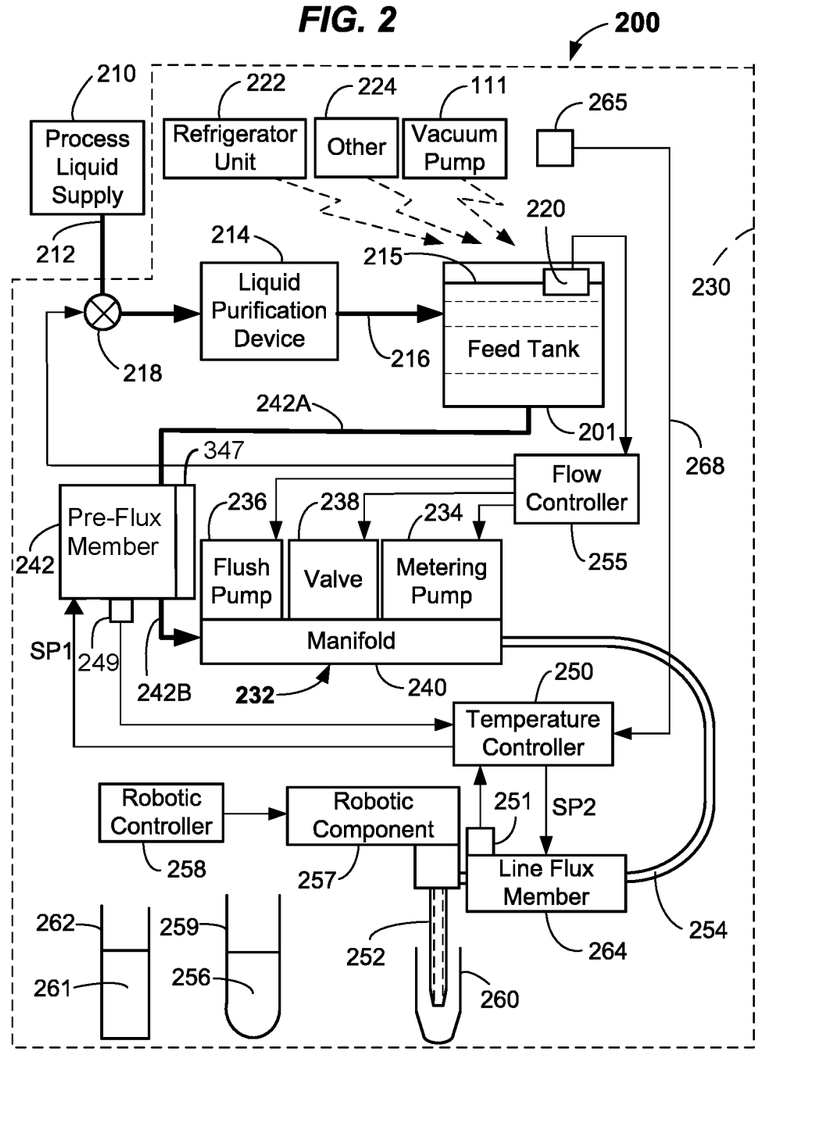
FIG. 2 illustrates a block diagram of a temperature-controlled process liquid delivery system according to embodiments.

In accordance with a first embodiment, as best shown in FIG. 2, a temperature-controlled process liquid delivery system 200 adapted to be used in an instrument (e.g., an immunoassay instrument, clinical analyzer, or the like) is described. The temperature-controlled process liquid delivery system 200 may be referred to as the "temperature-controlled process liquid delivery system" or "process liquid delivery system" or "liquid delivery system." The temperature-controlled process liquid delivery system 200 may be coupled to, or be part of, a precision metering system of an instrument or analyzer, and may deliver precisely-metered and temperature controlled volumes of one or more liquids from a probe. The liquid delivery system 200 may be provided as a subsystem in a larger system in which delivery of liquids having precisely-controlled process liquid temperatures are desired.

In more detail, a flow of a liquid (e.g., water) for the liquid delivery system 200 may be provided and delivered from a process liquid supply 210 in process liquid inflow 212. The process liquid supply 210 may be a city or private water supply, a water tank, a well, or the like. The process liquid inflow 212 (e.g., a conduit) may be fluidly connected and coupled to a liquid purification device 214.

The liquid purification device 214 may be any device or collection of devices that functions to filter and/or otherwise purify the liquid supplied so as to provide a flow of process liquid 215 (e.g., purified water) to a feed tank 201 to be contained therein. Liquid purification device 214 and the feed tank 201 may be connected and fluidly coupled by a conduit 216. The liquid purification device 214 may include one or more pretreatment devices, a reverse osmosis device, UV ionization, polishing, degassing, one or more particulate or other filters, and/or other conventional devices and/or treatments for filtering and/or purifying the process liquid 215 (e.g., water) to a relatively-high level of purity.

For example, the liquid purification device 214 may remove organics, chemical elements, minerals, particles or sediment, dissolved oxygen, or other contaminants from the process liquid 215. The process liquid 215 may then be used in the instrument or analyzer to dilute liquid samples, prepare reagents (e.g., where the process liquid 215 is added to a solid or powdered reagent material), as a backing liquid to dispense and/or aspirate liquid reagents (e.g., concentrated reagents), as a backing liquid to aspirate or dispense biological liquid specimens, as a process liquid to wash sample containers, and/or clean probes, for example. The liquid purification device 214 may also include various conduits, valves, accumulators, and other components. The purification level of the process liquid 215 may be to ASTM/NCCLS standards (e.g., NCCLS—National Committee on Clinical Laboratory Standards).

For example, the process liquid 215 may be purified to a level that is suitable for dispensing in a metering apparatus that is adapted to be used for aspiration and/or dispensing in the testing of analytes or other substances or characteristics in a biological liquid (e.g., blood, plasma and/or serum, urine, spinal fluid, interstitial fluid, cerebral fluid, or the like). For example, the purity may be sufficient to meet the standards for ASTM/NCCLS Type 1-IV and/or Type A-C, for example. Preferably, ASTM/NCCLS Type 1 and Type A purity standards may be provided by the liquid purification device 214. Other purity levels may be used.

The flow condition through the process liquid inflow 212 of process fluid 215 into the liquid delivery system 200 and to the liquid purification device 214 may be controlled via a valve 218, such as any suitable valve (e.g., a solenoid valve). Other types of valves may be used. As shown, the liquid purification device 214 is part of the instrument. However, it may be in a separate device or even in a separate room in some embodiments.

As process liquid 215 in the feed tank 201 is used by the instrument, process liquid 215 may be replenished in the liquid delivery system 200. Replenishment may be dictated by a level sensor 220 (e.g., a float type sensor) situated at an appropriate level within the feed tank 201. Other types of level sensors may be used. The valve 218 may be opened and a fresh supply of process liquid 215 may be allowed to enter into the liquid delivery system 200. Other suitable means for replenishment may be used. The process liquid 215 may be used, for example, in a metering apparatus 232, which is part of the liquid delivery system 200. In the depicted embodiment, the process liquid 215 is water. However, other process liquids may be used.

Again referring to FIG. 2, heat (depicted by jagged, dotted arrows) from one or more components of the instrument, such as refrigerator unit 222, vacuum pump 111, and/or other components 224 may be generated within the housing 230 of the instrument (indicated as a dotted line). Accordingly, the interior of the instrument housing 230 may be subject to fairly rapid temperature fluctuations during use. Changes in ambient temperature to which the instrument is exposed may further aggravate these temperature fluctuations. Similarly, the temperature of the water in the feed tank 201 may vary significantly over time.

The temperature-controlled process liquid delivery system 200 includes a metering apparatus 232 fluidly coupled to the feed tank 201. The metering apparatus 232 may be adapted to dispense a precise amount of a temperature-controlled process fluid 215 or otherwise aspirate or dispense a liquid specimen, liquid reagent, acid, base, or other liquid by using the process liquid 215 as the vehicle (liquid backing) for carrying out the aspiration and dispense. In some embodiments, the process liquid 215 may be used as a diluting agent in an assay process or other testing process. The assay or other process may be used to determine an amount of an analyte, component or characteristic in a liquid specimen (e.g., a biological liquid specimen), for example.

The metering apparatus 232 may include a metering pump 234 that is configured and adapted to precisely meter relatively smaller volumes of the process liquid 215 or other liquids as described above, such as in a volume of less than about 25 μL, by using the process liquid 215 as a liquid backing. The metering apparatus 232 may include a flush pump 236 that is configured and adapted to precisely dispense relatively larger volumes of the process liquid 215, to carry out a washing operation to flush the one or more of the system components (e.g., probe 252). In other embodiments, by activating valve 238 and metering pump 234 precise volumes of process liquid up to about 400 μl can be delivered. One or more valve(s) 238 may be used to switch between the pumps 234, 236 and a manifold 240 may be provided at suitable locations for accomplishing flow distribution of the process liquid 215. The manifold 240 may be a distribution manifold containing multiple internal passages connecting the pumps 234, 236 and the one or more valve(s) 238 to the respective outlet conduit 242B and metering line 254. Other constructions of the metering apparatus 232 may be used. For example, the metering apparatus 232 may include only a single pump and possibly a valve in some embodiments. Similarly, the manifold 240 may be replaced by conduits. Any suitable metering apparatus construction may be used.

The temperature-controlled process liquid delivery system 200 also includes a pre-flux member 242 positioned between the feed tank 201 and the metering apparatus 232. The pre-flux member 242 may be fluidly coupled to the feed tank 201 by conduit 242A and to the metering apparatus 232 by another conduit 242B. In one or more embodiments, the pre-flux member 242 may be positioned as close as possible to the metering apparatus 232 by shortening or eliminating the conduit 242B, i.e., by connecting the pre-flux member 242 directly to the manifold 240, for example.

Figure 3A:
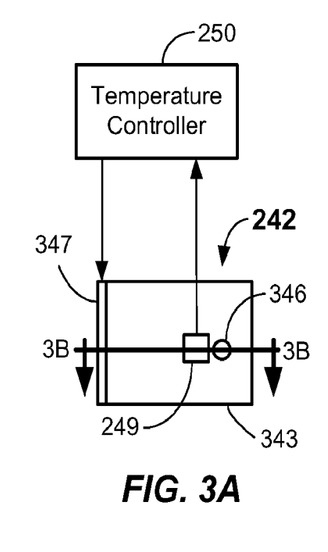
FIGS. 3A and 3B illustrate various views of a pre-flux member of a temperature-controlled process liquid delivery system according to embodiments.
Figure 3B:
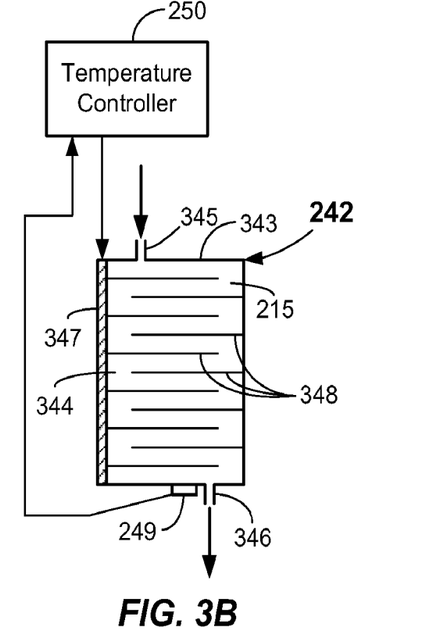

In one or more embodiments, the pre-flux member 242 may be a water bath device such as is shown in FIGS. 3A-3B. The pre-flux member 242 is adapted to control a temperature of the process liquid 215 that is received at the metering apparatus 232, such as at a manifold 240 thereof.

The pre-flux member 242 is thermally coupled to a flow path containing a process liquid 215 and located between a feed tank 201 and the metering apparatus 232.

Referring to FIG. 3A-3B, the pre-flux member 242 may include a container 343 including walls defining an internal chamber 344. Process liquid 215 may flow in through an inlet 345 and out through an outlet 346 of the pre-flux member 242. A temperature of one or more outer surfaces of the container 343 may be controlled by a flux element 347. Flux element 347 as used herein means a device that may heat, cool, or both. Examples of a flux element 347 are a film heater, resistive heater, or other suitable heating device. In other embodiments, the flux element 347 may be a Peltier device or a Thermoelectric Device (TED) that may function to heat, cool, or both. Thus, in some embodiments, heat may be added, extracted (cooled) by the pre-flux member 242. Multiple flow restrictors 348 may be provided in the internal chamber 344 to restrict process liquid flow so that a temperature of the process liquid 215 may be sufficiently controlled to a desired first temperature set point SP1 when exiting the pre-flux member 242 at the outlet 346. Outlet 346 is fluidly coupled to the metering apparatus 232 such as by the outlet conduit 242B.

The flux element 347 may be electrically coupled to a temperature controller 250 in one or more embodiments. The first temperature set point SP1 of the pre-flux member 242 may be controlled by the temperature controller 250. Feedback to the temperature controller 250 on whether the first set point SP1 has been achieved may be provided by pre-flux member sensor 249 located near an outlet 346 of the pre-flux member 242, for example. Temperature controller 250 may include a suitable microprocessor, power supply, conditioning electronics, A/D converters, and drivers to appropriately drive the flux element 347 to the desired first temperature set point SP1. The first set point SP1 may be determined by reference to a lookup table, a function, or other means stored in memory, for example.

Again referring to FIG. 2, the temperature-controlled process liquid delivery system 200 also includes a probe 252 fluidly coupled to the metering apparatus 232 by a length of metering line 254. The metering line 254 may be a flexible material, such as a plastic tube (e.g., a Telfon material) having an inside diameter of about 60 mm and a length of between about 1.2 m and 1.5 m, for example. Other dimensions and materials may be used. The probe 252 may include a tube with Teflon liner which is adapted to aspirate and/or dispense a biological liquid specimen, a liquid reagent, an acid, a base, or other liquid, and/or dispense the temperature-controlled process liquid 215 (e.g., purified water). The metering line 254 may be fluidly connected to the metering pump 234 by the manifold 240. In another embodiment, the metering line 254 may be directly connected to the metering pump 234 or valve 238. In the depicted embodiment, the flow control of temperature-controlled process fluid 215 to the metering line 254 may be achieved through control of one or more valve(s) 238 and operation of the metering pump 234 or the flush pump 236 by suitable control signals (designated by arrowed lines) received from a flow controller 255. Volume aspiration and dispensing may be precisely accomplished by counting steps of stepper motors coupled to the pump(s) 234, 236, for example. Other means for controlling aspirate and dispense volume may be used, such as a displacement sensor or the like.

Testing may involve accurately aspirating and dispensing of a biological liquid specimen, liquid reagent, another liquid, and/or the process liquid 215. To accomplish this, the metering pump 234 should be capable of precisely metering process liquid 215 with relatively high accuracy in either a dispensing mode and/or an aspirating mode. For example, in some embodiments the metering pump 234 should be able to meter to a volumetric accuracy of at least about +/−0.02 µL or less. However, in other embodiments, pump precision and volumetric accuracy are less important and temperature of the process liquid and liquid components at the start of each aspiration of the assay is controlled.

In one operational method according to an aspect of the invention, the probe 252 may be used to aspirate and dispense a biological liquid specimen 256 and/or process fluid 215. For example, in the above-mentioned "chase method," a robotic component 257 operable based upon control signals from a robotic controller 258 may position the probe 252 into a sample container 259 containing a volume of biological liquid specimen 256 (e.g., blood or a blood component or other liquid as described herein). The metering pump 234 may then draw (aspirate) a small volume of the biological liquid specimen 256 into the channel of the probe 252 from the sample container 259 via appropriate signals from the flow controller 255, move the probe 252 via operation of the robotic component 257, and transfer (dispense) at least some or all of that small amount of the biological liquid specimen 256 into a test vessel 260 (e.g., a cuvette).

During the act of dispensing, the temperature-controlled process fluid 215 is fluidly coupled to, and in thermal contact with, the biological liquid specimen 256 contained in a probe 252. Operation of the metering pump 234 causes flow of the temperature-controlled process fluid 215 in the metering line 254, and, thus, flow of biological liquid specimen 256 fluidly coupled thereto and possibly abutting therewith (or possibly separated by a small air bubble). This biological liquid specimen dispensing may be chased by operating the metering pump 234 and dispensing a volume of the process fluid 215 through the metering line 254 and probe 252 and into the test vessel 260. Similarly, the probe 252 (or a different probe and metering apparatus utilizing the process fluid 215 as a liquid vehicle) may also aspirate and dispense liquid reagent 261 from a reagent vessel 262 if needed for the testing operation, and dispense the liquid reagent into the test vessel 260. Other or different liquids may be aspirated and dispensed and transferred to the test vessel by the liquid delivery system 200. It should be recognized that, not only is the temperature of the process liquid 215 in the metering line 254 important because it is being dispensed, but the process liquid temperature thus may affect the temperature of the other liquids dispensed that it is in contact with, which may affect assay testing accuracy.

Figure 4A:
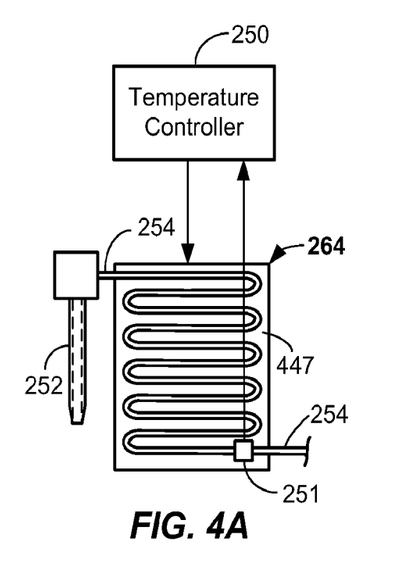
FIGS. 4A and 4B illustrate various views of a line flux member of a temperature-controlled process liquid delivery system according to embodiments.
Figure 4B:
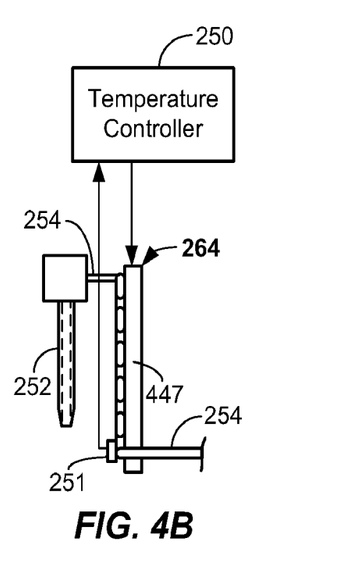
Figure 5:
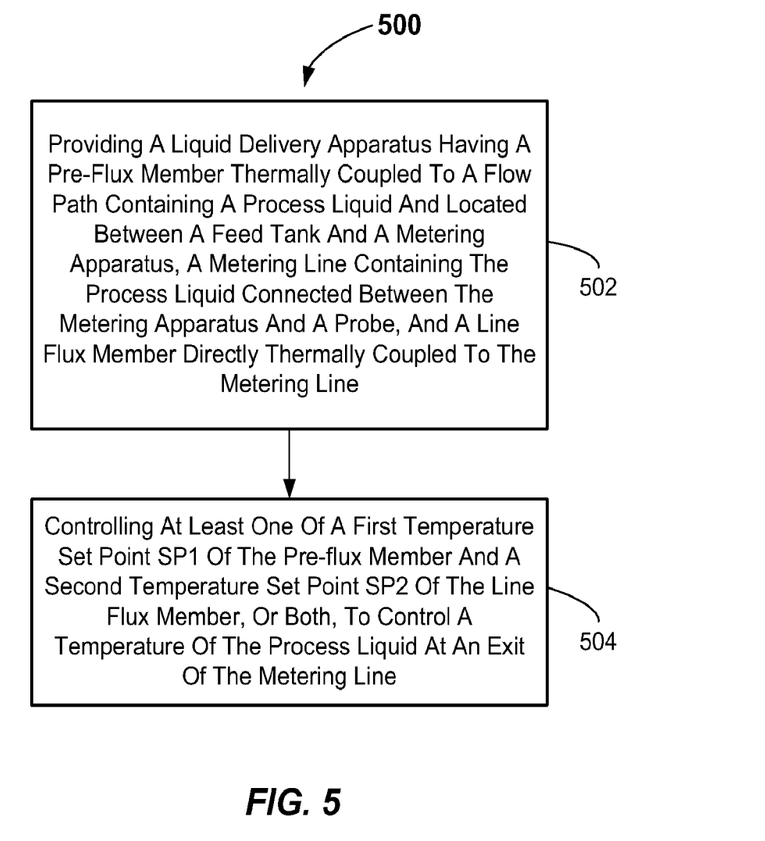
FIG. 5 is a flowchart illustrating a method of providing a temperature-controlled process liquid according to embodiments.

To further control the temperature of the process liquid 215, the temperature-controlled process liquid delivery system 200 also includes a line flux member 264. The line flux member 264 is provided in direct thermal contact with the metering line 254 and thus may accomplish a change in temperature thereof. In one or more embodiments, the line flux member 264 may be provided directly next to the probe 252 (e.g., within about 5 cm of the probe 252). The line flux member 264 may be adapted to thermally act upon (e.g., heat, cool, or both) the metering line 254 located between the metering apparatus 232 and the probe 252. In some embodiment, the line flux member 264 may act thermally upon less than all of the metering line 254. For example, the line flux member 264 may be thermally coupled to between about 10% to about 30% of a total length of the metering line 254. A second set point SP2 of the line flux member 264 may be set by the temperature controller 250. Feedback to the temperature controller 250 on whether the second set point SP2 has been achieved at the output of the line flux member 264 may be provided by line flux member sensor 251 located near an outlet 346 of the line flux member 264, for example. The line flux member 264 may be any suitable heat-imparting device, such as a bent-line thermal device, as shown in FIGS. 4A-4B, for example. Other types of line flux members 264 may be used.

The line flux member 264 may include a plurality of bends, coils, wraps, or overlapping sections that provide a long length (e.g., 3 m or more) of liquid passage within a relatively small area (e.g., less than about 200 cm$^2$), and between about 20 cm$^2$ and about 200 cm$^2$ in some embodiments. As shown in FIG. 4B, the length of liquid passage in the line flux member 264 may comprise multiple parallel sections, winds wraps or the like that are arranged on a flux element 447 such as thin foil or other resistive heater. Optionally, the flux element 447 may be a Peltier device or a TED as discussed above wherein heating, cooling, or both of the liquid 215 in the metering line 254 may be accomplished by the line flux member 264.

Operation of the metering pump 234 to either aspirate or dispense causes flow of the process liquid 215 in the metering line 254 and, thus, flow of any liquid fluidly coupled thereto and abutting therewith. Accordingly, temperature drift in an assay and/or dispensing accuracy when dispensing/aspirating liquid may be improved by precisely controlling a temperature of the process liquid 215 in the metering line 254, and especially at an exit thereof.

Operation of the temperature-controlled process liquid delivery system 200 to precisely control a temperature of the process liquid 215 at an exit from the metering line 254 will now be described. The temperature controller 250 of the liquid delivery system 200 is adapted to set the first temperature set point SP1 of the pre-flux member 242 and the second temperature set point SP2 of the line flux member 264. The respective set points SP1, SP2 may be set between limits based upon the effectiveness of the flux elements 347, 447 and the designs of the pre-flux member 242 and the line flux member 264. In one or more embodiments, one or more of the set points SP1, SP2 may be changed responsive to a received signal input from a temperature sensor 265 in input line 268. The temperature sensor 265 may be a thermocouple, thermistor, resistive temperature device (RDT), or the like. Other suitable types of temperature sensors may be used. The temperature sensor 265 may be provided within the instrument housing 230 at any suitable location that is representative of a transient operating temperature within the instrument. For example, the sensor 265 may be located in the reagent dispensing area.

One or both of the temperature set points SP1, SP2 may be adjusted according to a predefined control scheme or schedule. One goal of the control scheme or schedule may be to provide a substantially constant process liquid temperature at an exit of the metering line 254 (e.g., at the probe 252), for example. This may control temperature drift of the liquid assay components (e.g., biological liquid over time, and thus lead to more accurate test results. For example, it may be desired to maintain a temperature of the probe 252 at the within about +/−2 degrees C., or even +/−1 degrees C. from a selected nominal output temperature at the start of any aspiration and dispense operation. For example, the first and second set point values SP1, SP2 may be set to provide a nominal temperature of the metering line 254 that exits into the probe 252 at the start of the aspiration of the biological liquid 256. Controlling the nominal temperature of the metering line 254 that exits into the probe 252 at the start of the aspiration may result in a minimizing an amount of temperature drift for the assay testing for any particular input temperature at the temperature sensor 265. Such settings for SP1, SP2 may be determined by a designed experiment. One or both of the set point values SP1, SP2 may be adjusted to achieve the desired goal.

For example, in some cases, a schedule of the set point values SP1, SP2 may be established based upon a designed experiment for various sensed temperatures at the temperature sensor 265. For each sensed temperature at the temperature sensor 265, various SP1, SP2 values may be set, the experiment may be run, and the results of the temperature at the exit to the probe 252 and the results for a particular assay or test may be noted. Accordingly, based upon the noted results and within the ranges of SP1 and SP2 that are achievable by the liquid delivery system 200, predetermined settings for SP1, SP2 may be set. Such SP1, SP2 settings may be stored in a look-up table, curve fitted and represented in one or more equations or functions of the temperature at the temperature sensor 265, or other means.

Accordingly, in use, and upon receiving input from the temperature sensor 265, SP1 and SP2 settings may be selected from the range of available values to achieve a desired output temperature at an exit from the metering line 254, to minimize a level of environmental drift, or to achieve a level of testing precision. For example, in some embodiments the set point values SP1, SP2 may be set approximately equal to each other (SP1=SP2). In other embodiments, the set point values SP1, SP2 may be set unequal to each other. For example, if the instrument has run for some time and the sensed temperature in the housing from the temperature sensor 265 is relatively high, and the temperature of the process liquid 215 in the feed tank 201 is relatively low, then SP1 and SP2 may be set so that SP1>SP2. In other embodiments, SP2>SP1.

Before any aspiration of liquid biological liquid specimen, liquid reagent, or other liquid, depending upon the test being run, process liquid 215 may be used to carry out a probe washing operation to flush the probe 252. Even in this probe washing operation, embodiments of the present invention may be adapted to precisely control a temperature of the process liquid 215 in the metering line 254 by setting one or both of the set points SP1, SP2 so that the exit from the metering line 254 and thus the temperature of the probe 252, that is located close by, is set to a suitable nominal operating temperature, such that it is ready for the next aspiration in the sequence and/or the next test. In particular, the setting of the temperature of the process liquid 215 at the exit of the metering line 254 at the end of a probe washing operation may be to a predetermined nominal temperature value that is selected and establishing responsive to a measured temperature from the temperature sensor 265. According to a method aspect, a method of providing a temperature-controlled process liquid according to one or more embodiments will now be described with reference to FIG. 5. The method 500 includes, in 502, providing a liquid delivery apparatus (e.g., liquid delivery system 200) having a pre-flux member (e.g., 242) thermally coupled to a flow path containing a process liquid (e.g., 215) and located between a feed tank (e.g., 201) and a metering apparatus (e.g., 232), a metering line (e.g., 254) containing the process liquid (e.g., 215) connected between the metering apparatus (e.g., 232) and a probe (e.g., 252), and a line flux member (e.g., 264) directly thermally coupled to the metering line (e.g., 254), and in 504, controlling at least one of a first temperature set point SP1 of the pre-flux member (e.g., 242), and a second temperature set point SP2 of the line flux member (e.g., 264), or both, to control a temperature of the process liquid (e.g., 215) at an exit of the metering line (e.g., 254).

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed, but, to the contrary, the intention is to cover all modifications, equivalents, and alternatives falling within the scope of the invention.

What is claimed is:

1. A temperature-controlled process liquid delivery system for medical specimen testing of analytes or other substances or characteristics in a biological liquid, comprising:
    a feed tank containing a process liquid;
    a metering apparatus comprising a pump fluidly coupled to the feed tank, the metering apparatus configured to meter the process liquid in volumes ranging from 400 µL to 10 µL within a volumetric accuracy of +/−0.02 µL;
    a flow path between the feed tank and the metering apparatus;
    a pre-flux member operative to heat and to cool the process liquid, the pre-flux member comprising a first flux element positioned directly adjacent to the metering apparatus and thermally coupled to the flow path, the first flux element comprising a first heater;
    a metering line fluidly coupled to the metering apparatus;
    a probe fluidly coupled to the metering apparatus by the metering line;
    a line flux member operative to heat and to cool the process liquid, the line flux member comprising a second flux element directly thermally coupled to the metering line and located directly adjacent to the probe, the second flux element comprising a second heater; and
    a temperature controller operatively connected to the pre-flux member and the line flux member to control a temperature of the process liquid at an exit of the metering line.

2. The temperature-controlled process liquid delivery system of claim 1, wherein the line flux member is thermally coupled to between about 10% and about 30% of a total length of the metering line to control a temperature of less than all of the metering line between the metering apparatus and the probe.

3. The temperature-controlled process liquid delivery system of claim 1, further comprising a pre-flux temperature sensor coupled to the pre-flux member and a line flux temperature sensor coupled to the line flux member, the temperature controller operatively connected to sense an input temperature from each of the pre-flux and line flux temperature sensors.

4. The temperature-controlled process liquid delivery system of claim 3, wherein the temperature controller is programmed to drive the first flux element to establish a first set point SP1 of at least the pre-flux member.

5. The temperature-controlled process liquid delivery system of claim 3, wherein the temperature controller is programmed to drive the second flux element to establish a second set point SP2 of at least the line flux member.

6. The temperature-controlled process liquid delivery system of claim 1, wherein the temperature controller is programmed to establish a first set point SP1 of the pre-flux member and a second set point SP2 of the line flux member.

7. The temperature-controlled process liquid delivery system of claim 1, comprising a robotic component, wherein the probe is coupled to and moveable by the robotic component.

8. A temperature-controlled liquid delivery apparatus for medical specimen testing of analytes or other substances or characteristics in a biological liquid, comprising:
    a feed tank;
    a metering apparatus configured to meter a process liquid in volumes ranging from 400 µL to 10 µL within a volumetric accuracy of +/−0.02 µL;
    a flow path between the feed tank and the metering apparatus;
    a probe;
    a pre-flux member operative to heat and to cool the process liquid, the pre-flux member comprising a first flux element thermally coupled to the flow path and located directly adjacent to the metering apparatus, the first flux element comprising a first heater;
    a metering line connected between the metering apparatus and the probe;
    a line flux member operative to heat and to cool the process liquid, the line flux member comprising a second flux element directly thermally coupled to the metering line and located directly adjacent to the probe, the second flux element comprising a second heater; and
    a temperature controller operatively connected to the pre-flux member and the line flux member to control a temperature of the process liquid at an exit of the metering line.

9. The liquid delivery apparatus of claim 8, wherein the temperature controller is operatively connected to the first flux element and the second flux element to control a first set point SP1 of the pre-flux member and a second set point SP2 of the line flux member.

10. The liquid delivery apparatus of claim 9, comprising one or more temperature sensors, wherein the temperature controller is operatively connected to the one or more temperature sensors to select the first set point SP1 and the second set point SP2 based upon measured temperature from the one or more temperature sensors.

11. The liquid delivery apparatus of claim 10, wherein the one or more temperature sensors comprise a housing temperature sensor, the liquid delivery apparatus further comprising a housing containing at least the metering apparatus, the metering line, and the housing temperature sensor, wherein the measured temperature comprises a temperature inside of the housing.

12. The liquid delivery apparatus of claim 8, wherein the pre-flux member comprises an internal chamber that includes the process liquid and multiple flow restrictors, wherein the first flux element is operative to heat or cool the process liquid contained within the internal chamber.

13. A method of providing a temperature-controlled process liquid for medical specimen testing of analytes or other substances or characteristics in a biological liquid, comprising:
    providing a liquid delivery apparatus including a feed tank, a process liquid, a metering apparatus configured to meter the process liquid in volumes ranging from 400 µL to 10 µL within a volumetric accuracy of +/−0.02 µL, a probe, a flow path, a pre-flux member operative to heat and to cool the process liquid, the pre-flux member thermally coupled to the flow path containing the process liquid and located directly adjacent to the metering apparatus, the pre-flux member comprising a first heater, a metering line containing the process liquid connected between the metering apparatus and the probe, and a line flux member operative to heat and to cool the process liquid, the line flux member directly thermally coupled to the metering line and located directly adjacent to the probe, the line flux member comprising a second heater; and controlling a first temperature set point SP1 of the pre-flux member and a second temperature set point SP2 of the line flux member to control a temperature of the process liquid at an exit of the metering line.

14. The method of claim 13, wherein the liquid delivery apparatus further includes a temperature sensor and the controlling comprises establishing the first temperature set point SP1 of the pre-flux member and the second temperature set point SP2 of the line flux member responsive to a measured temperature from the temperature sensor that is representative of a transient operating temperature.

15. The method of claim 14, wherein the measured temperature comprises a temperature that is representative of a transient operating temperature inside of a housing of an instrument containing the liquid delivery apparatus.

16. The method of claim 13, wherein the controlling a first temperature set point SP1 of the pre-flux member and a second temperature set point SP2 of the line flux member comprises setting the first temperature set point SP1 and the second temperature set point SP2 to be approximately equal.

17. The method of claim 13, wherein the controlling a first temperature set point SP1 of the pre-flux member and a second temperature set point SP2 of the line flux member comprises setting the first temperature set point SP1 and the second temperature set point SP2 to be unequal.

18. The method of claim 13, comprising setting the temperature of the process liquid at the exit of the metering line to a predetermined nominal value with a temperature controller upon a metering pump of the metering apparatus drawing a volume of liquid in an aspiration and dispense operation.

19. The method of claim 18 comprising establishing the predetermined nominal temperature responsive to a measured temperature from a temperature sensor located in a housing containing the liquid delivery apparatus.

* * * * *